United States Patent
Nguyen-Ba

(12) 
(10) Patent No.: US 6,545,001 B2
(45) Date of Patent: Apr. 8, 2003

(54) ANTIVIRAL NUCLEOSIDE ANALOGUES

(75) Inventor: Nghe Nguyen-Ba, Quebec (CA)

(73) Assignee: BioChem PHARMA, Inc., Quebec (CA)

( * ) Notice: Subject to any disclaimer, the term of this patent is extended or adjusted under 35 U.S.C. 154(b) by 0 days.

(21) Appl. No.: 09/893,605

(22) Filed: Jun. 29, 2001

(65) Prior Publication Data

US 2001/0049372 A1 Dec. 6, 2001

Related U.S. Application Data

(63) Continuation of application No. 09/468,813, filed on Dec. 22, 1999, now Pat. No. 6,358,963.
(60) Provisional application No. 60/113,797, filed on Dec. 23, 1998.

(51) Int. Cl.[7] .................. A01N 43/90; A61K 31/519
(52) U.S. Cl. ................ 514/262.1; 514/263.1; 514/264.1; 514/264.11; 544/276; 544/277
(58) Field of Search ............... 514/262, 263, 514/264; 544/276, 277

(56) References Cited

U.S. PATENT DOCUMENTS

| | | | |
|---|---|---|---|
| 4,000,137 A | 12/1976 | Dvonch et al. | 260/252 |
| 4,041,037 A | 8/1977 | Dvonch et al. | 260/256 |
| 4,336,381 A | 6/1982 | Nagata et al. | 544/313 |
| 4,415,573 A | 11/1983 | Ochi et al. | 424/251 |
| 4,960,773 A | 10/1990 | Korbonits et al. | 514/234.21 |
| 5,041,449 A | 8/1991 | Belleau et al. | 514/274 |
| 5,047,407 A | 9/1991 | Belleau et al. | 514/274 |
| 5,179,104 A | 1/1993 | Chu et al. | 544/310 |
| 5,204,466 A | 4/1993 | Liotta et al. | 544/317 |
| 5,210,085 A | 5/1993 | Liotta et al. | 514/274 |
| 5,270,315 A | 12/1993 | Belleau et al. | 514/262 |
| 5,276,151 A | 1/1994 | Liotta et al. | 544/317 |
| 5,444,063 A | 8/1995 | Schinazi | 514/262 |
| 5,539,116 A | 7/1996 | Liotta et al. | 544/317 |
| 5,684,010 A | 11/1997 | Schinazi | 514/266 |
| 5,700,937 A | 12/1997 | Liotta et al. | 544/317 |
| 5,767,122 A | 6/1998 | Chu et al. | 514/262 |
| 5,792,773 A | 8/1998 | Chu et al. | 514/274 |
| 5,814,639 A | 9/1998 | Liotta et al. | 514/274 |
| 5,830,898 A | 11/1998 | Schinazi | 514/262 |
| 5,834,474 A | 11/1998 | Schinazi | 514/262 |
| 5,852,027 A | 12/1998 | Liotta et al. | 514/274 |
| 5,869,461 A | 2/1999 | Cheng et al. | 514/43 |
| 5,914,331 A | 6/1999 | Liotta et al. | 514/274 |
| 5,914,400 A | 6/1999 | Liotta et al. | 544/314 |
| 5,925,643 A | 7/1999 | Chu et al. | 514/262 |

FOREIGN PATENT DOCUMENTS

| | | | | |
|---|---|---|---|---|
| EP | 071926 A | 7/1982 | ............ | C07H/19/16 |
| EP | 0337713 | 10/1989 | ......... | C07D/473/32 |
| EP | 0382526 | 8/1990 | ......... | C07D/473/00 |
| EP | 0515144 | 5/1992 | ......... | A61K/31/505 |
| EP | 0515156 | 5/1992 | ............ | C07H/19/04 |
| EP | 0515157 | 5/1992 | ......... | C07D/327/04 |
| WO | WO 90/01492 | 2/1990 | ......... | C07H/19/073 |
| WO | WO 91/17159 | 11/1991 | ......... | C07D/411/04 |
| WO | WO 92/08717 | 5/1992 | ......... | C07D/409/04 |
| WO | WO 92/10496 | 6/1992 | ......... | C07D/475/00 |
| WO | WO 92/10497 | 6/1992 | ......... | C07D/475/00 |
| WO | WO 92/14729 | 9/1992 | ......... | C07D/411/04 |
| WO | WO 92/14743 | 9/1992 | | |
| WO | WO 92/18517 | 10/1992 | ............ | C07H/17/00 |
| WO | WO 92/19246 | 11/1992 | .......... | A61K/31/70 |
| WO | WO 92/20669 | 11/1992 | ......... | C07D/327/04 |
| WO | WO 97/21706 | 7/1993 | ......... | C07D/411/04 |
| WO | WO 94/14802 | 7/1994 | ......... | C07D/411/04 |
| WO | WO 93/13778 | 6/1997 | .......... | A61K/31/70 |

OTHER PUBLICATIONS

Pascal J. Bolon et al. "Novel Isomeric Dideoxynucleosides as Potential Antiviral Agents," *Tetrahedron*, vol. 50, No. 26, pp. 7747–7764 (1994).

Susan M. Daluge, Steven S. Good and Wayne H. Miller, "Abacavir (1592), a second–generation nucleoside HIV reverse transcriptase inhibitor," International Antiviral News 6:7, International Medical Press 1998.

Zhengxian, Gu et al., "Mechanism of Action and In Vitro Activity of 1',3'–Dioxolanylpurine Nucleoside Analogues against Sensitive and Drug–Resistant Human Immunodeficiency Virul Type 1 Variants," Antimicrobial Agents and Chemotherapy, Oct. 1999, vol. 43, No. 10, pp. 2376–2382.

Hea O. Kim et al., "1,3–Dioxolanylpurine Nucleosides (2R,4R) and with Selective Anti–HIV–1 Activity in Human Lymphocytes," *J. Med. Chem.*, vol. 36, No. 1, pp. 30–37 (1993).

(List continued on next page.)

*Primary Examiner*—James O. Wilson
*Assistant Examiner*—Patrick Lewis
(74) *Attorney, Agent, or Firm*—Millen, White, Zelano & Branigan, P.C.

(57) ABSTRACT

The invention relates to cis-nucleosides of formula (I):

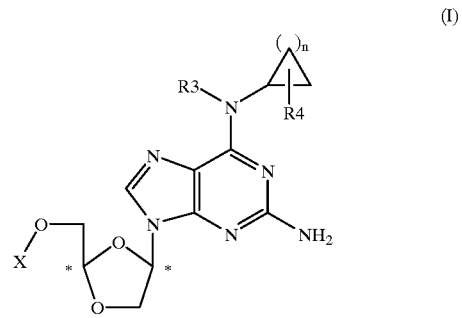

and pharmaceutically acceptable salts thereof, wherein X, $R_3$, $R_4$ and are as defined herein. The nucleosides can be in racemic form or in the form of their (+) or (−) enantiomers. The compounds are useful for treating HBV and/or HIV infections, alone or in combination with other therapeutic agents.

87 Claims, 1 Drawing Sheet

OTHER PUBLICATIONS

M. Arshad Siddiquie et al., "Antiviral Optically Pure Dioxolane Purine Nucleoside Analogues," Biorganic & Medicinal Chemistry letters, vol. 3, No. 8, pp. 1543–1546, 1993.

Belleau et al., Abstract No. M.C.P. 63, V International Conference on AIDS, The Scientific and Social Challenge, Montreal, Quebec, Canada, Jun. 4–9, 1989.

Chun K. Chu et al. "Asymmetric Synthesis of Enantiomerically Pure (−)–(1'R, 4'R)–Dioxolane–thymine and Its Anti–HIV Activity," Tetrahedron Letters, vol. 32, No. 31, pp. 3791–3794, 1991.

Daniel W. Norbeck et al., "A New 2',3'–Dideoxynucleoside Prototype With In Vitro Activity Against HIV," Tetrahedron Letters, vol. 30, No. 46, pp. 6263–6266, 1989.

Chung K. Chu et al., "Pharmacokinetics of (−)–β–D–2, 6–diaminopurine dioxolane and its metabolite, dioxolane guanosine, in woodchucks (Marmota monax)," Antiviral Chemistry & Chemotherapy (1996) 7(2), pp. 62–70.

P. Rajagopalan et al., "Pharmacokinetics of (−)–β–D–2,6 Diaminopurine Dioxolane and its metabolite Dioxolane Guanosine in Rhesus Monkeys," Abstract PPDM 8195, Pharmaceutical Research, Supplement No. 11, pp. 381–386 (1994).

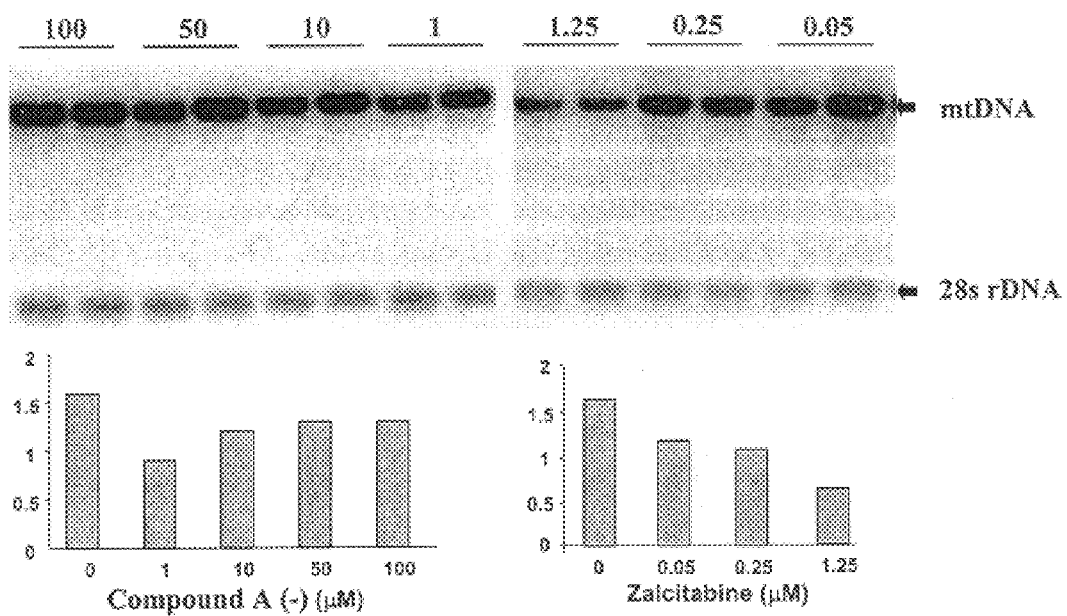
Figure 1. Mitochondria DNA toxicity assay of the compound A (-)

ANTIVIRAL NUCLEOSIDE ANALOGUES

This application is a continuation of U.S. Ser. No. 09/468,813 filed Dec. 22, 1999 issued as U.S. Pat. No. 6,358,963. This application claims priority from U.S. No. 60/113,797 filed Dec. 23, 1998 which is herein incorporated by reference.

FIELD OF THE INVENTION

The present invention relates to novel purine nucleoside analogues useful as antiviral agents. Particularly, the invention relates to purine nucleosides with improved pharmacokinetic properties.

BACKGROUND OF THE INVENTION

In the United States, more than 12 million new cases of sexually transmitted diseases (STDs) occur each year. Of the top 10 reportable diseases in the United States, five are STDs including chlamydia, gonorrhea, syphilis, the Acquired Immune Deficiency Syndrome (AIDS) and hepatitis B virus (HBV) infection of which AIDS and HBV infection have no cures.

In the case of AIDS, the World Health Organization predicts that by the year 2000 there will be 40 million people worldwide infected with the human immunodeficiency virus (HIV), the virus that causes (AIDS). Hepatitis infections affect 5 times more people that HIV. It has been reported by the World Health Organization that 2000 million people alive today are infected with HBV virus, of whom 350 million are chronically infected and therefore at risk of death from liver disease.

Although mortality rates from AIDS are dropping due to new therapies, AIDS remains the second leading cause of death in adults between the ages of 29 and 40. Combination anti-HIV therapy is now the standard of care for people with HIV. There are now 11 anti-HIV drugs available by prescription. These anti-HIV drugs fall into three categories: nucleoside analogs, which include zidovudine, didanosine, zalcitabine, stavudine or lamivudine; protease inhibitors which include indinavir, nelfinavir, saquinavir and ritonavir and non-nucleoside reverse transcriptase inhibitors (NNRTI) which include nevirapine, delavirdine and efavirenz. Compared to HIV, there is presently only few licensed therapy for chronic hepatitis B virus infection which are interferon and lamivudine. Other drugs are currently under clinical trials including, famciclovir, lobucavir and adefovir. But many studies have shown that most patients relapse after completion of therapy and develop resistance to the drugs.

Development of resistance has recently become a major concern in the treatment of HIV and HBV infections. Resistance usually occurs when the drugs being used are not potent enough to completely stop virus replication. If the virus can reproduce at all in the presence of drugs, it has the opportunity to make changes in its structure, called mutations, until it finds one that allows it to reproduce in spite of the drugs. Once a mutation occurs, it then grows undetected and soon is the dominant strain of the virus in the individual. The drug becomes progressively weaker against the new strain. There is also increasing concern about cross-resistance. Cross-resistance occurs when mutations causing resistance to one drug also cause resistance to another. Several studies have proven that combining two drugs delays the development of resistance to one or both drugs compared to when either drug is used alone. Other studies suggest that three-drug combinations extend this benefit even further. As a result, many people believe that the best way of preventing, or at least delaying resistance is to use multi-drug combination therapies. But as the number of drugs increases, so does the risk or drug interactions and toxicity.

One way to increase the efficacy of a drug is to improve its pharmacokinetic properties which contribute to its therapeutic activity. The science of pharmacokinetics is the study of the factors which determine the amount of chemical agents at their sites of biological effect at various times after the application of an agent or drug to biological systems. Pharmacokinetics includes study of drug absorption and distribution ("biotranslocation"), study of the chemical alterations a drug may undergo in the body ("biotransformation"), and study of the means by which drugs are stored in the body and eliminated from it. In chronic drug therapy, bioavailability is the more important factor because it relates to the extent to which a drug is absorbed and reaches the bloodstream or is otherwise available to the treatment site in the body. The bioavailability is directly linked to the drug ability to dissolve in biological fluids.

(−)-β-D-2,6-diaminopurine dioxolane (DAPD) and (−)-β-D-1,3-dioxolane guanine (DXG) have been reported to have a high efficacy against HIV-1 in various cell systems, minimal cross resistance with lamivudine and low toxicity. However, these compounds have poor pharmacokinetic properties which could be improved. It would therefore be useful to be provided with compounds having improved pharmacokinetics for use in the treatment of patients infected with HIV and HBV.

SUMMARY OF THE INVENTION

In one aspect, the present invention provides novel purine cis-nucleoside compounds represented by formula (I):

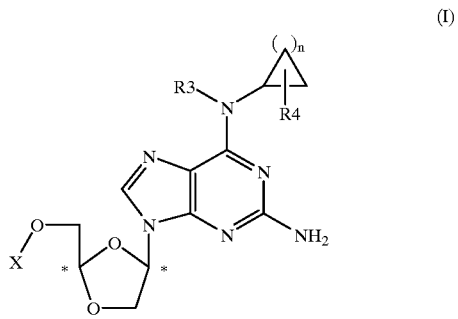

(I)

and pharmaceutically acceptable salts thereof,
wherein:

n is 1 or 2

$R_4$ is chosen from H, COOH, CONH$_2$, OH, SH, NH$_2$, NO$_2$, $C_{1-6}$ alkyl, $C_{2-6}$ alkenyl, $C_{2-6}$ alkynyl, halogen, COR$_a$ wherein R$_a$ is a $C_{1-6}$ alkyl, $C_{2-6}$ alkenyl, $C_{2-6}$ alkynyl or COOR$_b$, wherein R$_b$ is a $C_{1-6}$ alkyl, $C_{2-6}$ alkenyl, or $C_{2-6}$ alkynyl;

$R_3$ is H or a $C_{1-6}$ alkyl, $C_{2-6}$ alkenyl, $C_{2-6}$ alkynyl;

X is chosen from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, or $$-\overset{\overset{\displaystyle O}{\|}}{\underset{\displaystyle ORc}{P}}-ORc$$

wherein each Rc is independently chosen from H, $C_{1-6}$ alkyl, $C_{2-6}$ alkenyl, $C_{2-6}$ alkynyl or an hydroxy protecting group; and wherein said nucleoside is present in the form of the (−) enantiomer, the (+) enantiomer and mixtures thereof, including racemic mixtures.

The compounds of the present invention are useful in therapy, in particular as antivirals.

In another aspect, there is provided a method of treating viral infections in a subject in need of such treatment comprising administering to the subject a therapeutically effective amount of a compound or composition of the invention.

In another aspect, there is provided a pharmaceutical formulation comprising the compound of the invention in combination with a pharmaceutically acceptable carrier or excipient.

Still another aspect, there is provided a method of treating viral infections in a subject in need of such treatment comprising administering to the subject a combination comprising at least one compound according to formula I and at least one further therapeutic agent chosen from nucleoside analogues; non nucleoside reverse transcriptase inhibitors (NNRTIs); or protease inhibitors.

In still another aspect, there is provided a pharmaceutical formulation comprising at least one compound according to formula I, at least one further therapeutic agent chosen from nucleoside analogues; nonnucleoside reverse transcriptase inhibitors (NNRTIs); or protease inhibitors, and a pharmaceutically acceptable carrier or excipient.

In another aspect of the invention is the use of a compound according to formula I, for the manufacture of a medicament for the treatment of viral infections.

A BRIEF DESCRIPTION OF THE DRAWINGS

FIG. 1 illustrates the results of a Mitochondria toxicity assay of compound A (−) in HepG2 cells as described in Example 18.

DETAILED DESCRIPTION OF THE INVENTION

In one embodiment, compounds of the present invention comprise those wherein the following embodiments are present, either independently or in combination.

In one embodiment X is H.

Alternatively X is $$-\overset{\overset{\displaystyle O}{\|}}{\underset{\displaystyle ORc}{P}}-ORc$$

wherein each Rc is independently chosen from H, $C_{1-6}$ alkyl, $C_{2-6}$ alkenyl, $C_{2-6}$ alkynyl or an hydroxy protecting group chosen from S-acylthioethyl ester, acyloxymethyl ester or alkyl methyl carbonate. In a further embodiment, X is $$-\overset{\overset{\displaystyle O}{\|}}{\underset{\displaystyle ORc}{P}}-ORc$$

wherein each Rc is independently an hydroxy protecting group chosen from acetyl-2-thioethyl ester, pivaloyloxymethyl ester or isopropyloxycarbonyloxymethyl ester.

In one embodiment, n is 1.
In a further embodiment, $R_3$ is H or methyl.
In a further embodiment, $R_3$ is H.
In a further embodiment $R_4$ is chosen from H, COOH, CONH$_2$, $C_{1-6}$ alkyl, $C_{2-6}$ alkenyl, $C_{2-6}$ alkynyl or COOR$_b$ wherein R$_b$ is a $C_{1-6}$ alkyl, $C_{2-6}$ alkenyl, or $C_{2-6}$ alkynyl.
In a further embodiment $R_4$ is H, COOH, or $C_{1-6}$ alkyl.
In a further embodiment $R_4$ is H, COOH, methyl or ethyl.
In a further embodiment $R_4$ is methyl or ethyl.
In an alternative embodiment, $R_4$ is COOH.
In a further embodiment $R_4$ is H.
In a further embodiment, $R_3$ is H or methyl and $R_4$ is H.
In a further embodiment $R_4$ and $R_3$ are H.

In one embodiment, the compounds of the present invention are represented by formula (Ia):

(Ia)

and pharmaceutically acceptable salts thereof, wherein each of X, $R_3$ and $R_4$ are as defined above.

It will be appreciated by those skilled in the art that the compounds of formula (I) and (Ia) contain at least two chiral centres which are marked by an asterisk (*) on the general formula (I) and (Ia). The compounds of formula (I) and (Ia) thus exist in the form of two different optical isomers (i.e. (+) or (−) enantiomers or β-L and β-D). All such enantiomers and mixtures thereof including racemic mixtures are included within the scope of the invention. The single optical isomer or enantiomer can be obtained by method well known in the art, such as chiral HPLC, enzymatic resolution and chiral auxiliary, or can be stereoselectively synthesized.

In accordance with the present invention there is provided compounds with improved pharmacokinetic properties According to one embodiment of the present invention there is provided compounds with improved bioavailability.

According to a further embodiment of the present invention there is provided a method of treating a viral infection in a subject in need of such treatment comprising administering to the subject a therapeutically effective amount of a compound of formula I or a pharmaceutically acceptable salt thereof.

According to another embodiment of the present invention there is provided a method of treating a retroviral infection in a subject in need of such treatment comprising administering to the subject a therapeutically effective amount of a compound of formula I or a pharmaceutically acceptable salt thereof.

According to a further embodiment of the present invitation there is provided a method of treating a subject infected by the HIV virus comprising administering to the subject a therapeutically effective amount of a compound of formula I or a pharmaceutically acceptable salt thereof.

According to a further embodiment of the present invention there is provided a method of treating a subject infected by the HRV virus comprising administering to the subject a therapeutically effective amount of a compound of formula I or a pharmaceutically acceptable salt thereof.

Compounds in accordance with the present invention include:

Compound A cis-2-hydroxymethyl-4-(2'-amino-6'-cyclopropylamino-purine-9'-yl)-1,3-dioxolane

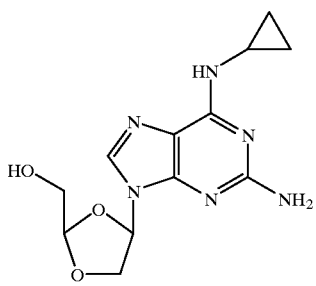

Compound B cis-2-hydroxymethyl-4-(2'-amino-6'-cyclobutylamino-purine-9'-yl)-1,3-dioxolane

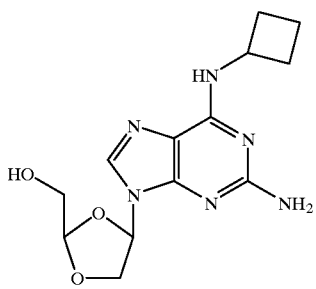

Compound C cis-2-hydroxymethyl-4-(2'-amino-6'-[1-carboxylic acid-cyclopropylamino]-purine-9'-yl)-1,3-dioxolane

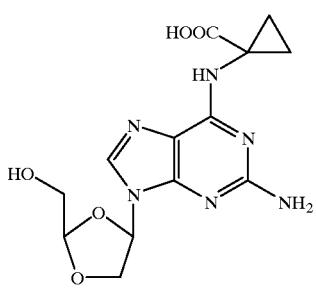

In a further embodiment, compounds of the invention include:

Compound A(−) (−)-(2R, 4R)-2-hydroxymethyl-4-(2'-amino-6'-cyclopropylamino-purine-9'-yl)-1,3-dioxolane

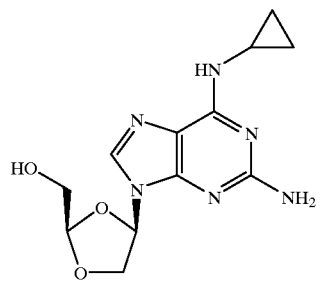

Compound B(−) (−)-(2R, 4R)-2-hydroxymethyl-4-(2'-amino-6'-cyclobutylamino-purine-9'-yl)-1,3-dioxolane

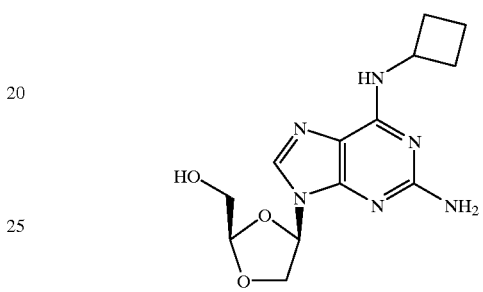

Compound C(−)(−)-(2R, 4R)-2-hydroxymethyl-4-(2'-amino-6'-[1-carboxylic acid-cyclopropylamino]-purine-9'-yl)-1,3-dioxolane

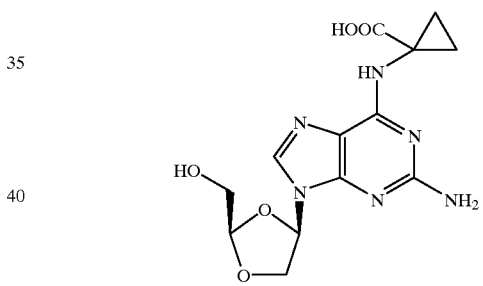

In one embodiment, the compound of the present invention are in the form of the (+) enantiomer at least 95% free of the corresponding (−) enantiomer.

In one embodiment, the compound of the present invention are in the form of the (+)enantiomer at least 97% free of the corresponding (−) enantiomer.

In one embodiment, the compound of the present invention are in the form of the (+) enantiomer at least 99% free of the corresponding (−) enantiomer.

In one embodiment, the compound of the present invention are in the form of the (−) enantiomer at least 95% free of the corresponding (+) enantiomer.

In one embodiment, the compound of the present invention are in the form of the (−) enantiomer at least 97% free of the corresponding (+) enantiomer.

In one embodiment, the compound of the present invention are in the form of the (−) enantiomer at least 99% free of the corresponding (+) enantiomer.

In one embodiment, the compound of the present invention is Compound A

In one embodiment, the compound of the present invention is compound A (−).

There is also provided a pharmaceutically acceptable salts of the present invention. By the term pharmaceutically acceptable salts of compounds of general formula (I) and (Ia) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

References hereinafter to a compound according to the invention includes compounds of the general formula (I) and (Ia) and there pharmaceutically acceptable salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

When there is a sulfur atom present, the sulfur atom can be at different oxydation level, S, SO, or $SO_2$. All such oxydation level are within the scope of the present invention.

Halogen herein means fluoro, chloro, bromo, and iodo, for example, fluoro.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or (Ia) or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The compounds of the invention may also be used in combination with other antiviral agents.

In one embodiment, combinations of the present invention comprise those wherein the following embodiments are present, either independently or in combination.

In one embodiment, the compounds of the invention may be employed together with at least one other antiviral agent is chosen from nucleoside analogues, NNRTI or protease inhibitors.

In one embodiment, the nucleoside analogues is a 1,3 oxathiolane analogue.

In a further embodiment, the 1,3 oxathiolane analogue is lamivudine, coviracil or 2-hydroxymethyl-4-(cytosin-1'-yl)-1,3-oxathiolane.

In a further embodiment, the 1,3 oxathiolane analogue is 2-hydroxymethyl-4-(cytosin-1'-yl)-1,3-oxathiolane.

In a further embodiment, the 1,3 oxathiolane analogue is 2R-hydroxymethyl-4R-(cytosin-1'-yl)-1,3-oxathiolane.

In a further embodiment, the 1,3 oxathiolane analogue is 2S-hydroxymethyl-4S-(cytosin-1'-yl)-1,3-oxathiolane.

In one embodiment, the compounds of the invention may be employed together with at least one other antiviral agent is chosen from zidovudine, didanosine, zalcitabine, stavudine, lamivudine, nevirapine, delavirdine, efavirenz, indinavir, nelfinavir, saquinavir or ritonavir.

In one embodiment, the compounds of the invention may be employed together with at least one other antiviral agent chosen from nevirapine, efavirenz, zidovudine, stavudine, or lamivudine.

In one embodiment, the compounds of the invention may be employed together with at least one other antiviral agent chosen from efavirenz, zidovudine, stavudine, or lamivudine.

In one embodiment, the compounds of the invention may be employed together with at least one other antiviral agent chosen from efavirenz, zidovudine or lamivudine.

In one embodiment, the compounds of the invention are employed together with efavirenz, zidovudine or lamivudine. In one embodiment, the compounds of the invention may be employed together with at least one other antiviral agent chosen from nevirapine, zidovudine, stavudine, or lamivudine.

In one embodiment, the compounds of the invention are employed together with nevirapine, zidovudine, stavudine, and lamivudine.

In one embodiment, the compounds of the invention may be employed together with at least one other antiviral agent is chosen from zidovudine, stavudine, or lamivudine.

In one embodiment, the compounds of the invention are employed together with zidovudine, stavudine, or lamivudine.

In one embodiment, the compounds of the invention may be employed together with zidovudine.

In one embodiment, the compounds of the invention may be employed together with stavudine.

In one embodiment, the compounds of the invention may be employed together with lamivudine.

In one embodiment, the compounds of the invention may be employed together with nevirapine.

In one embodiment, the compounds of the invention may be employed together efavirenz.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) and (Ia) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The ratio between the compounds of the present invention and the second therapeutic agent will be readily appreciated by those skilled in the art. For example, one may use from about 1:1 to about 1:50 of compounds of the invention:second therapeutic agent. In a further embodiment, one may use from about 1:1 to about 1:30 of compounds of the invention:second therapeutic agent In a further embodiment, one may use from about 1:1 to about 1:20 of compounds of the invention:second therapeutic agent. In a further embodiment, one may use from about 1:1 to about 1:15 of compounds of the invention:second therapeutic agent. In a further embodiment, one may use from about 1:1 to about 1:10 of compounds of the invention:second therapeutic agent. In a further embodiment, one may use from about 1:1 to about 1:5 of compounds of the invention:second therapeutic agent. In a further embodiment, one may use from about 1:1 to about 1:3 of compounds of the invention:second therapeutic agent. If a further therapeutic agent is added, ratios will be adjusted accordingly.

The compounds of the present invention can be prepared as follows.

The following examples are provided to illustrate various embodiments of the present invention and shall not be considered as limiting in scope.

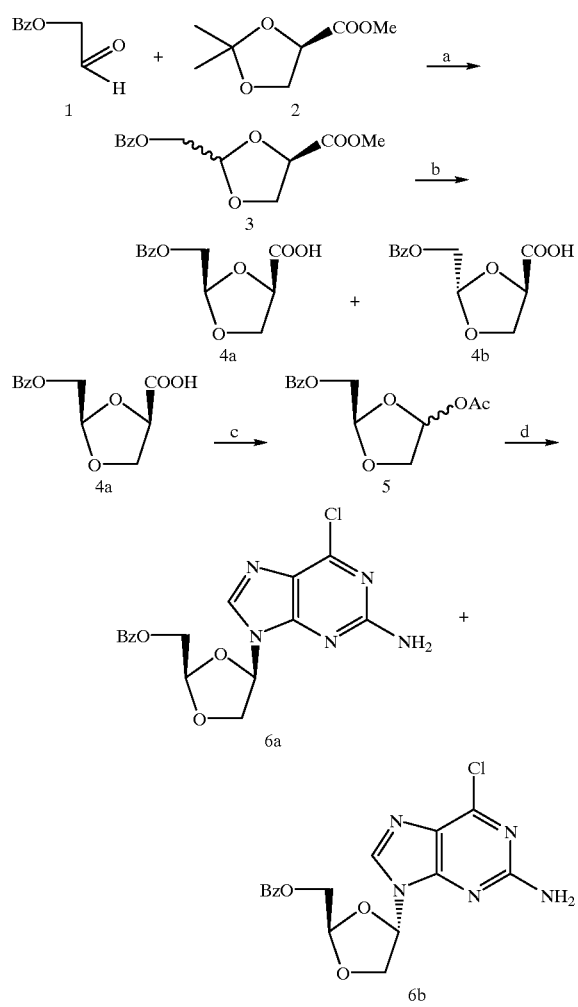

a) PTSA. 100° C., neat; b) LiOH,MeOH—H₂O; c) Pb(OAc)₄, MeCN, pyridine; d) TMSTf, CH₂Cl₂, TMS-6-Cl-guanine, 80%; e) EtOH, cyclopropyl amine, 80° C.; f) NH₃, MeOH The target compound can be prepared according to the above scheme:

Step a: 2-benzoyloxy-acetaldehyde 1 reacted with methyl (R)-(+)-2,2-dimethyl-1,3-dioxolane-4-carboxylate 2 in the presence para-toluene sulfonic acid (pTSA) under transketalisation to give 2-benzoyloxymethyl-1,3-dioxolane-4-carboxylmethyl ester 3 as a mixture of cis and trans isomers in a ratio of 3:1 in favor of cis isomer.

Step b: The carboxylic methyl ester 3 was selectively hydrolysed using lithium hydroxide to give the corresponding acid derivatives 4a and 4b. The mixture were separated by flash chromatography and each isomer was further used independently.

Step c: The carboxylic function of 4a was then converted to an acetoxy leaving group by treatment with lead tetraacetate.

Step d: The (2R)-2-benzoyloxymethyl-1,3-dioxolane-4-acetoxy 4a was coupled with silylated 2-amino-6-chloropurine using trimethylsilyl trifluoromethylsulfonate (TMSTf) as activator to give a mixture of cis and trans isomers of nucleoside analogues 6a and 6b in a ratio of 1.2:1 in favor of cis isomer. The mixture was separated by flash chromatography and each isomer was used independently further.

Step e: The (−)-(2R, 4R)-2-benzoyloxymethyl-4-(2'-amino-6'-chloro-purine-9'-yl)-1,3-dioxolane 6a was treated with cyclopropylamine in ethanol to give the corresponding (−)-(2R, 4R)-2-benzoyloxymethyl-4-(2'-amino-6'-cyclopropylamino-purine-9'-yl)-1,3-dioxolane 7 in good yield.

Step f: Removal of benzoyl protecting group was achieved by treatment of (−)-(2R, 4R)-2-benzoyloxymethyl- 4-(2'-amino-6'-cyclopropylamino-purine-9'-yl)-1,3-dioxolane 7 with methanolic ammonia to give the desired product (−)-(2R, 4R)-2-hydroxymethyl-4-(2'-amino-6'-cyclopropylamino-purine-9'-yl)-1,3-dioxolane A in good yield.

EXAMPLE 1

Methyl-2-(R, S)-benzoyloxymethyl-1,3-dioxolane-4-(R)-carboxlate

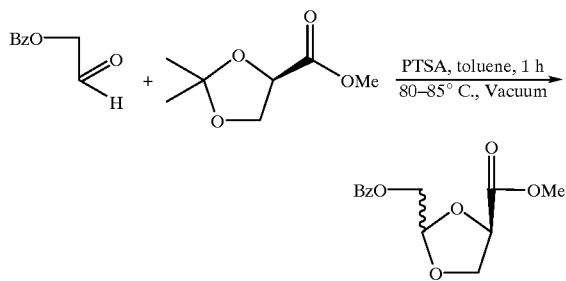

To a solution of methyl-2,3-O-isopropylidene-D-glycerate (Fluka: cat #|59449), (9.76 g, 60.9 mmol, 1 eq) and benzoyloxyacetaldehyde (10 g, 60.9 mmol, 1 eq) in toluene (20 mL) at 80° C., p-toluenesulfonic acid (460 mg, 2.4 mmol, 4 mol %) was added. The reaction flask was kept under vacuum for one hour and a distillate was collected (80–85° C.) during this peroid of time. The residue was then cooled to RT and purified by column chromatography on silica gel, using hexanes/ethylacetate as eluent to produce 13.2 g (81%) of the title compound as a mixture of cis and trans isomers in a ratio of 3:1.

Cis isomer:
$^1$H-NMR (CDCl$_3$): δ(ppm): 3.75 (s, 3H, CH3); 4.15(dd, 1H, C$_5$—CH), 4.30 (dd, 1H, C$_5$—CH); 4.5 (m, 2H, CH$_2$—O—CO—C$_6$H$_5$); 4.7 (m, 1H, C$_4$—CH); 5.4 (t, 1H, C$_2$—CH); 7.45–8.1 (m, 5H, Ar—CH).

Trans isomer:
$^1$H-NMR (CDCl$_3$): δ(ppm): 3.8 (s, 3H, CH$_3$); 4.1(dd, 1H, C$_5$—CH); 4.35 (dd, 1H, C$_5$—CH); 4.45 (m, 2H, CH$_2$—O—CO—C$_6$H$_5$); 4.75 (m, 1H, C$_4$—CH); 5.5 (t, 1H, C$_2$—CH); 7.45–8.1 (m, 5H, Ar—CH).

EXAMPLE 2

(2R, 4R)-2-benzoyloxymethyl-1,3-dioxolane-4-carboxylic acid (2S, 4R)-2-benzoyloxymethyl-1,3-dioxolane-4-carboxylic acid

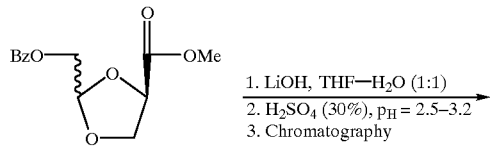

To a solution of methyl-2-(R, S)-benzoyloxymethyl-1,3-dioxolane-4-(R)-carboxylate, (411 g, 1.54 mmol, 1 eq., 2:1 mixture of cis and trans isomers) in a 1:1 mixture of THF and water, lithium hydroxide (64.8 g, 1.54 moles, 1 eq) was added portionwise over a period of 30 min., keeping the reaction flask temperature below 30° C. After 90 min., THF was removed by vacuum and the aqueous solution was acidified to p$_H$ 2.5–3.2, by dropwise addition of 30% (w/w) sulphuric acid. The resulting solution was extracted with dichloromethane (4×400 mL). The combined organic phase was washed with brine, dried over sodium sulphate and concentrated to produce 380 g of a dark oil. The isomers were separated by column chromatography on silica gel, using 2% acetic acid in dichloromethane to produce 220 g of the cis isomer (56.5%) and 116 g of the trans isomer (30%). Each of isomers was independently used for next step.

Cis isomer:
(2R, 4R)-2-benzoyloxymethyl-1,3-dioxolane-4-carboxylic acid. $^1$H-NMR (CDCl$_3$): δ(ppm): 4.2 (t, 1H, C$_5$—H); 4.4 (m, 1H); 4.5 (m, 1H); 4.7 (m, 2H); 5.4 (t, 1H, C$_2$—CH); 7.45–8.1 (m, 5H, Ar—CH); 7.2–8.0(bs, 1H, COOH).

Trans isomer:
(2S, 4R)-2-benzoyloxymethyl-1,3-dioxolane-4-carboxylic acid. $^1$H-NMR (CDCl$_3$): δ(ppm): 4.15 (dd, 1H, C$_5$—H); 4.4 (t, 1H, C$_5$—H); 4.45 (m, 2H, CH$_2$—OCOC$_6$H$_5$); 4.8 (dd, 1H, C$_4$—CH); 5.6 (t, 1H, C$_2$—CH); 7.45–8.1 (m, 5H, Ar—CH); 8.3–8.8 (bs, 1H, COOH).

EXAMPLE 3

(2R)-2-benzoyloxymethyl-4-(R, S)-acetoxy-1,3-dioxolane

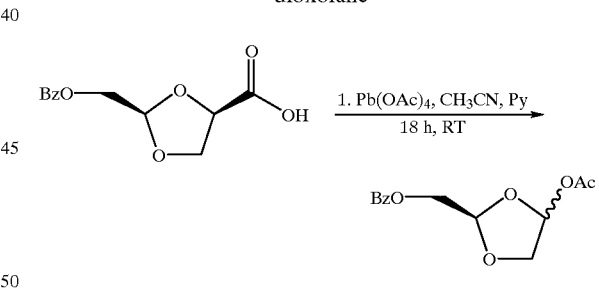

To a solution of (2R. 4R)-2-benzoyloxymethyl-1,3-dioxolane-4-carboxylic acid, (130 g, 0.515 moles, 1 eq) and pyridine (60 mL, 0.741 moles, 1.44 eq) in acetonitrile at 4° C., lead tetraacetate. (assay 95%, 300 g, 0.678 moles, 1.25 eq) was added over a period of 20 min. The reaction mixture was kept under stirring for 18 hours at RT. The inorganics were removed by filtration, the filtrate was poured on to a saturated solution of sodium bicarbonate (2 L) followed by addition of solid sodium bicarbonate (p$_H$=7–8). The organic phase was separated, and the aqueous phase was extracted with ethylacetate (3×400 mL). The combined organic phase was concentrated and purified by column chromatography, on silica gel, using hexanes/ethylacetate as eluent to produce 93.5 g (68%) of the title compound as a mixture of cis and trans isomers in a ratio of 2:1. The mixture was used for next step.

cis/trans isomers:

$^1$H-NMR (CDCl$_3$): δ(ppm): 2.0,2.15 (s, 3H, CH$_3$); 4.05–4.45 (m, 4H, CH); 5.45, 5.55 (t, 1H, C$_2$—CH); 6.4, 6.45 (dd, 1H, C$_4$—CH); 7.45–8.1 (m, 5H, Ar—CH);

EXAMPLE 4

(2R, 4R) and (2R, 4S)-2-benzoyloxymethyl-4-(2'-amino-6'-chloro-purine-9'-yl)-1,3-dioxolane

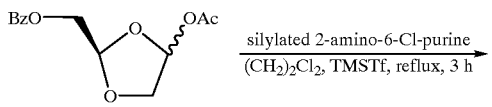

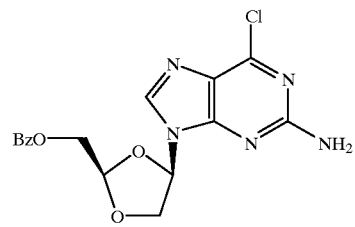

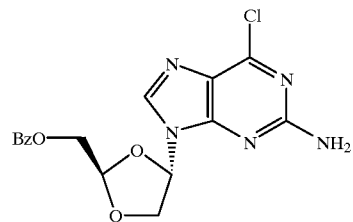

2-amino-6-chloro-purine (4.15 g, 1.3 eq.) in 50 ml of hexamethyldisilazane(HMDS) containing 100 mg of ammonium sulfate was heated under reflux for 3 h after which time the clear solution was evaporated to dryness in vacuo. The residue was dissolved in 100 ml of anhydrous 1,2-dichloroethane. (2R)-2-benzoyloxymethyl-4-acetoxy-1,3-dioxolane (5 g) was dried by co-evaporation twice with benzene (2×30 ml) and dissolved in 100 ml of anhydrous 1,2-dichloroethane. The solution was then transferred into the reaction flask containing silylated 2-amino-6-chloro-purine solution. The mixture was placed in a 60° C. preheated oilbath for 15 minutes, followed the addition of trimethylsilyl triflate (TMS-Tf, 3.8 ml, 1.1 eq.). The mixture was heated at refluxing under nitrogen for 3 h and the solution became brown. TLC (hex:EtOAc 7:3 for sugar and hex:EtOAc 1:4 for product) indicated a completed reaction with the disappearance of sugar and the presence of two well separated spots for cis and trans products. The reaction mixture was cooled to room temperature, poured into a saturated sodium bicarbonate solution (100 ml) and stirred for 10 minutes. The organic layer was collected and the aqueous layer was extracted twice with methylene chloride (2×50 ml). The combined organic solution was washed with water, brine and dried over MgSO$_4$ as usual. and solvent was evaporated to dryness to give a foam (7 g). H-NMR of the crude indicated clean reaction with cis and trans products in a ratio of 1.2:1 in favor of cis isomer. The crude product was purified on silica gel using a gradient of hexane:ethyl acetate 7:3, 1:1 and 2:3 as eluant to yield 2.5 g of trans isomer (less polar, α-anomer) as a foam, which was crystallized in EtOH and 3 g of cis isomer (more polar, β-anomer) as a foam, which was crystallized in EtOH and 0.3 g of mixture cis and trans in favor of cis as a foam for a total of 82% yield.

Trans isomer:

(+)-(2R, 4S)-2-benzoyloxymethyl-4-(2'-amino-6'-chloro-purine-9'-yl)-1,3-dioxolane R$_f$:0.40 (hexane-EtOAc 3:7)

[α$_D$] +21.16° (c 0.293 in CH$_2$Cl$_2$)

$^1$H-NMR (CDCl$_3$): δ(ppm): 4.45–4.55 (m, 4H ; C$_5$—H$_2$, C$_2$—CH$_2$—OBz), 5.16 (b, 2H, NH$_2$), 5.83 (t, 1H, C$_2$—H, J=3.8 Hz), 6.39 (dd, 1H, C$_4$—H), 7.45 (t, 2H, aromatic), 7.62 (t, 1H, aromatic), 7.92 (s, 1H, C$_8$·-8), 8.10 (d, 2H aromatic).

U.V.: (CH$_3$OH) λ$_{max}$: 312 nm

Cis isomer:

(−)-(2R, 4R)-2-benzoyloxymethyl-4-(2'-amino-6'-chloro-purine-9'-yl)-1,3-dioxolane R$_f$: 0.26 (hexane-EtOAc 3:7)

[α$_D$] −87.7° (c 0.2565 in CH$_2$Cl$_2$)

$^1$H-NMR (CDCl$_3$): δ(ppm): 4.25–4.33 dd, 1H, C$_5$—H), 4.60–4.64 (m, 3H; C$_5$—H and C$_2$—CH$_2$—OBz), 5.17 (b, 2H, NH$_2$), 5.42 (t, 1H, C$_2$—H, J=3.5 Hz), 6.33 (dd, 1H, C$_4$—H), 7.45 (t, 2H, aromatic), 7.62 (t, 1H, aromatic), 7.95 (d, 2H, aromatic), 8.05 (s, 1H, C$_8$·-8).

U.V.: (CH$_3$OH) λ$_{max}$: 312 nm.

EXAMPLE 5

(−)-(2R, 4R)-2-benzoyloxymethyl-4-(2'-amino-6'-cyclopropylamino-purine-9'-yl)-1,3-dioxolane

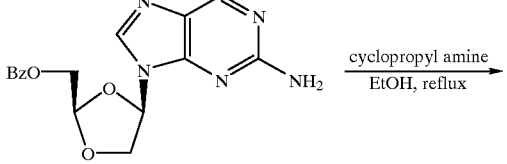

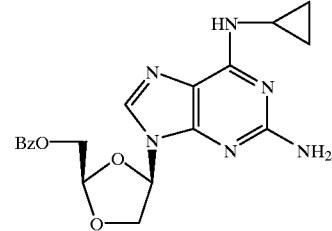

To a solution of (−)-(2R, 4R)-2-benzoyloxymethyl-4-(2'-amino-6'-chloro-purine-9'-yl)-1,3-dioxolane (600 mg) in ethanol (30 ml) was added cyclopropylamine (2 ml, =18 eq.). The mixture was gently heated at reflux (80–85° C.) for 18 h and cooled to room temperature. Solvent was evaporated to dryness in vacuo.

The residue was dissolved in 100 ml of methylene chloride, washed with saturated NaHCO$_3$ solution, water, brine and dried over MgSO$_4$. Solvent was removed in vacuo and residue was purified on silica gel using EtOAc:MeOH as eluant to give the desired product as a foam in 80% yield. (506 mg).

R$_f$: 0.26 (CH$_2$Cl$_2$: MeOH 95:5)

[α$_D$] −67.7° (c 0.2565 in CH$_2$Cl$_2$)

$^1$H-NMR (CDCl$_3$): δ(ppm): 0.64–0.68 (m, 2H, CH$_2$ of cyclopropyl), 0.91–0.96 (m, 2H, CH$_2$ of cyclopropyl), 3.06 (b, 1H, CH of cyclopropyl), 4.27–4.30 (dd, 1H, C$_5$—H), 4.54–4.57 (dd, 1H; C$_5$—H) 4.60 (t, 2H, C$_2$—CH$_2$—OBz), 5.37 (b, 2H, NH$_2$), 5.42 (t, 1H, C$_2$—H, J=3.5 Hz), 6.28 (b, 1H, NH), 6.35 (dd, 1H, C$_4$—H), 7.45 (t, 2H, aromatic), 7.58 (t, 1H, aromatic) 7.77 (s, 1H, C$_{8'}$-8), 8.01(d, 2H, aromatic), U.V.: (CH$_3$OH) $\lambda_{max}$: 283 and 260 nm.

EXAMPLE 6

(−)-(2R, 4R)-2-hydroxymethyl-4-(2'-amino-6'-cyclopropylamino-purine-9'-yl)-1,3-dioxolane (compound A)

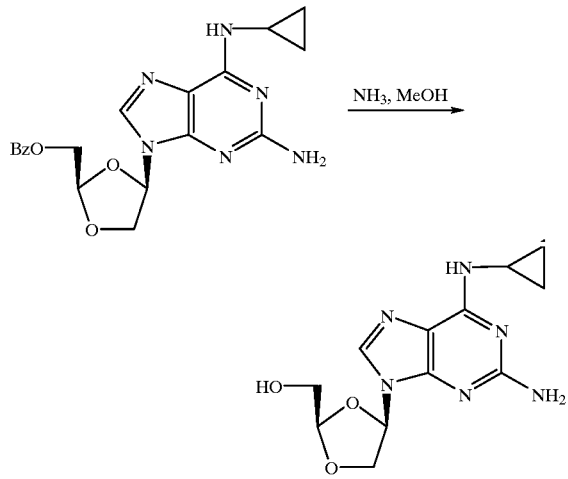

A solution of (−)-(2R, 4R)-2-benzoyloxymethyl-4-(2'-amino-6'-cyclopropylamino-purine-9'-yl)-1,3-dioxolane (480 mg) in 30 ml of saturated methanolic ammonia was stirred at room temperature for 18 h. The mixture was evaporated to dryness in vacuo. The residue was dissolved in 20 ml of water, washed twice with 10 ml of methylene chloride and lyophilized to give 283 mg of white solid in 80% yield.

R$_f$: 0.26 (CH$_2$Cl$_2$: MeOH 9:1)
[α$_D$] −35.9° (c 0.334 in MeOH)
$^1$H-NMR (DMSO$_{d-6}$): δ(ppm): 0.55 (m, 2H, CH$_2$ of cyclopropyl), 0.95 (m, 2H, CH$_2$ of cyclopropyl), 3.15 (b, 1H, CH of cyclopropyl), 3.80 (m, 2H, CH$_2$OH), 4.30 (dd, 1H, C$_5$H), 4.55 (dd, 1H ; C$_5$—H), 5.08 (t, 1H, C$_2$—H), 5.17 (b, H, OH), 6.15 (b, 2H, NH$_2$), 6.52 (dd, 1H, C$_4$—H), 7.72 (b, 1H, NH), 8.12 (s, 1H, C$_{8'}$-8)
U.V.: (CH$_3$OH) $\lambda_{max}$: 283 and 260 nm.

EXAMPLE 7

(−)-(2R, 4R)-2-benzoyloxymethyl-4-(2'-amino-6'-cyclobutylamino-purine-9'-yl)-1,3-dioxolane

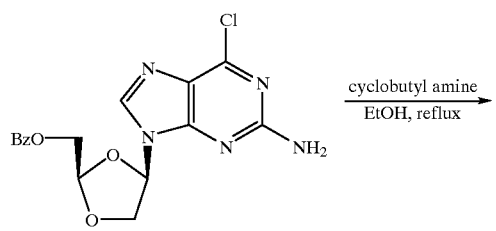

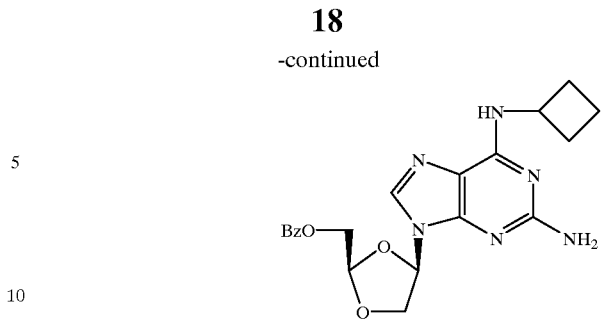

To a solution of (−)-(2R, 4R)-2-benzoyloxymethyl-4-(2'-amino-6'-chloro-purine-9'-yl)-1,3-dioxolane (250 mg) in ethanol (25 ml) was added cyclobutylamine (0.17 ml, =3 eq.). The mixture was gently heated at reflux (80–85° C.) for 18 h and cooled to room temperature. Solvent was evaporated to dryness in vacuo. The residue was dissolved in 100 ml of methylene chloride, washed with saturated NaHCO$_3$ solution, water, brine and dried over MgSO$_4$. Solvent was removed in vacuo and residue was purified on silica gel using EtOAc:MeOH 95:5 as eluant to give the desired product as a foam in 84% yield.(230 mg).

R$_f$: 0.31 (CH$_2$Cl$_2$: MeOH 95:5)
[α$_D$] −62.5° (c 0.4925 in CH$_2$Cl$_2$)
$^1$H-NMR (CDCl$_3$): δ(ppm): 1.74–1.78 (m, 2H, CH$_2$ of cyclobuyl), 1.95–2.00 (m, 2H, CH$_2$ of cyclobutyl), 2.43–2.45 (m, 2H, CH$_2$ of cyclobutyl), 4.27–4.30 (dd, 1H, C$_5$—H), 4.54–4.57 (dd, 1H ; C$_5$—H), 4.59 (t, 2H, C$_2$—CH$_2$—OBz), 4.75 (b, 1H, CH of cyclobutyl), 5.37 (b, 2H, NH$_2$), 5.41 (t, 1H, C$_2$—H, J=3.6 Hz), 6.00 (b, 1H, NH), 6.35 (dd, 1H, C$_4$—H), 7.45 (t, 2H, aromatic), 7.58 (t, 1H, aromatic), 7.75 (s, 1H, C$_{8'}$-8), 8.01(d, 2H, aromatic),
U.V.: (CH$_3$OH) $\lambda_{max}$: 283 and 263 nm.

EXAMPLE 8

(−)-(2R, 4R)-2-hydroxymethyl-4-(2'-amino-6'-cyclobutylamino-purine-9'-yl)-1,3-dioxolane (compound B)

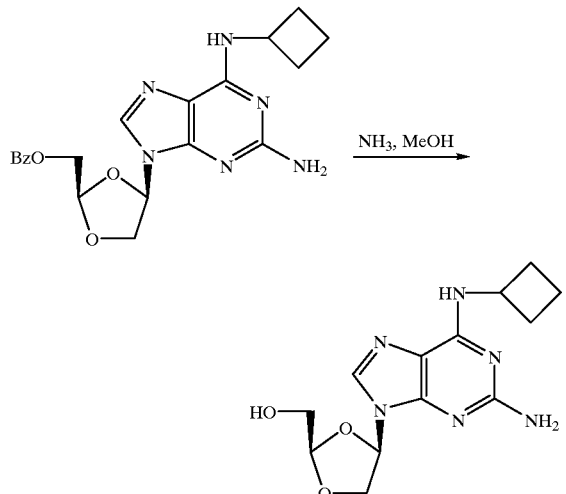

A solution of (−)-(2R, 4R)-2-benzoyloxymethyl-4-(2'-amino-6'-cyclobutylamino-purine-9'-yl)-1,3-dioxolane (214 mg) in 20 ml of saturated methanolic ammonia was stirred at room temperature for 18 h. The mixture was evaporated to dryness in vacuo. The residue was dissolved in 20 ml of water, washed twice with 10 ml of ether and evaporated to dryness by coevaporation with ethanol to give 154 mg of pure product as a foam in 96% yield.

$R_f$: 0.52 (CH$_2$Cl$_2$: MEOH 9:1)

[$\alpha_D$] −29.04° (c 0.396 in MeOH)

$^1$H-NMR (DMSO$_{d-6}$): δ(ppm): 1.61 (m, 2H, CH$_2$ of cyclobutyl), 2.06 (m, 2H, CH$_2$ of cyclobutyl), 2.18 (m, 2H, CH$_2$ of cyclobutyl), 3.58 (m, 2H, CH$_2$OH), 4.17 (dd, 1H, C$_5$—H), 4.40 (dd, 1H; C$_5$—H), 4.90 (b, 1H, CH of cyclobutyl), 5.01 (t, 1H, C$_2$—H), 5.42 (b, H, OH), 5.87 (b, 2H, NH$_2$), 6.19 (dd, 1H, C$_4$—H), 7.62 (b, 1H, NH), 7.85 (s, 1H, C$_{8'}$-8).

U.V.: (CH$_3$OH) $\lambda_{max}$: 283 and 260 nm.

EXAMPLE 9

(−)-(2R, 4R)-2-hydroxymethyl-4-(2'-amino-6'-{1-carboxylic acid-cyclopropylamino}-purine-9'-yl)-1, 3-dioxolane (compound C)

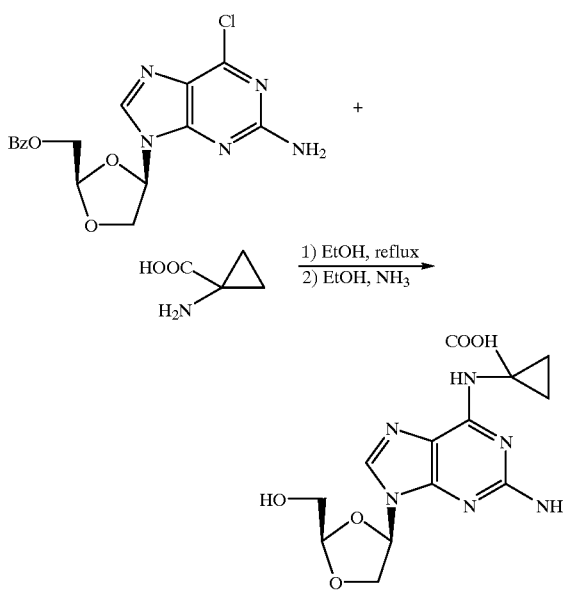

To a solution of (−)-(2R, 4R)-2-benzoyloxymethyl-4-(2'-amino-6'-chloro-purine-9'-yl)-1,3-dioxolane (210 mg) in ethanol (30 ml) was added 1-amino-1-cyclopropanecarboxylic acid (113 mg=2 eq.) and triethylamine (0.2 ml, 2.5 eq). The mixture was gently heated at reflux (80–85° C.) for 72 h and cooled to room temperature. Solvent was evaporated to dryness in vacuo. The residue was dissolved in methanolic ammonia (20 ml) and stirred for overnight. Solvent was removed in vacuo and residue was purified on silica gel using a gradient of CH$_2$Cl$_2$: MeOH 95:5 to 9:1 to remove by product and finally the desired product was eluted with CH$_2$Cl$_2$: MeOH 4:1 containing 0.5% of acetic acid. It gave 80 mg of pure product (42.5% yield.

$R_f$: 0.34 (CH$_2$Cl$_2$: MeOH 4:1 containing 0.5% AcOH)

$^1$H-NMR (DMSO$_{d6}$): δ(ppm): 1.05 (b, 2H, CH$_2$ of cyclopropyl), 1.45 (b, 2H, CH$_2$ of cyclopropyl), 3.58 (b, 2H, CH$_2$—OH), 4.17 (dd, 1H, C$_5$—H), 4.41 (dd, 1H; C$_5$—H), 5.12 (t, 1H, C$_2$—H), 5.15 (b, 1H, OH), 5.82 (b, 1H, NH), 6.19 (dd, 1H, C$_4$—H), 7.71 (b, H, NH), 7.86 (s, 1H, C$_{8'}$-8).

U.V.: (CH$_3$OH) $\lambda_{max}$: 283 and 264 nm.

EXAMPLE 10

Anti-HIV Activity

ANTIVIRAL ASSAYS. The anti-HIV-1 activity of the compound A (−) were assessed by employing HIV-1$_{IIIB}$ in a variety of cell types as previously described (Gu et al., 1992, 1994, 1999; Rando et al., 1995; Salomon et al., 1994). Briefly, cells were incubated with virus at a multiplicity of infection (MOI) of 0.005 for T cell assays and an MOI of 0.5 for monocytic cell assays for 3 hrs. Unbound virus was then removed by washing the cells, followed by seeding the cells into a 96-well plate. The infected cells were cultured in the presence of a serial concentrations of the test compound for 5–7 days. The anti-HIV-1 efficacy was determined by testing for HIV-1 RT activity or p24 level in the cell culture supernatants. All assays were performed in duplicate. Zidovudine and/or lamivudine were used as controls in each experiment.

Comparison of the compound A (−) with approved anti-HIV agents. The compound A (−) had 0.083 μM EC$_{50}$ against HIV-1$_{IIIB}$ in MT-2 cells, which is the same level of anti-HIV-1 activity as lamivudine, stavudine, zalcitabine and abacavir, but less activity than zidovudine (Table 1).

TABLE 1

Comparison of anti-HIV activity of the compound A (-) with approved antiretroviral agents (determined by RT activity)

| Compound | EC$_{50}$ (μM) ± S.D. in MT-2 cells |
|---|---|
| Compound A (−) | 0.082 ± 0.022 |
| DXG | 0.065 ± 0.039 |
| Zidovudine | 0.0051 ± 0.0025 |
| Lamivudine | 0.061 ± 0.028 |
| Stavudine | 0.38 ± 0.26 |
| Zalcitabine | 0.05 |
| Abacavir | 0.10 |

Activity of the compound A (−) against HIV-1 in various cells. Anti-HIV-1 activity of the compound A (−) were tested in different types of cells, including human peripheral monocyte cells (PBMCs), T-cell (MT-2 and MT-4) and monocytic cell (U937) lines. The compound A (−) had submicromolar EC$_{50}$s against HIV-1$_{IIIB}$ in different types of cells tested (Table 2).

TABLE 2

Anti-HIV-1 efficacy of the compound A (-) in various types of cells (determined by RT activity)

| | EC$_{50}$ (μM) | | |
|---|---|---|---|
| Cells | Compound A (−) | Zidovudine | Lamivudine |
| PBMCs (3)* | 0.22 | 0.0027 | 0.035 |
| MT-2 (4) | 0.082 | 0.0051 | 0.061 |
| MT-4 (2) | 0.14 | 0.015 | 0.17 |
| U937 (1) | 0.82 | 0.027 | 0.014 |

*Numbers in the brackets are no. of determinations.

Furthermore, antiretroviral activity of the compound A (−) was also assessed using different types of HIV-1 strains. Resuts in Table 3 showed that the compound A (−) was active against non-syncytium inducing (HIV-1$_{9881}$), dual tropic (HIV-1$_{macBAL}$) and monocytropic (HIV-1$_{WRM8488}$) strains.

TABLE 3

Anti-HIV activity of the compound A (−) against
different types of HIV-1 strains (determined by p24)

| Virus | Cells | EC$_{50}$ ($\mu$M) | |
|---|---|---|---|
| | | Compound A (−) | Zidovudine |
| HIV-1$_{9881}$ | PBMCs | 0.59 | 0.0017 |
| HIV-1$_{macBAL}$ | PBMCs | 4.14 | 0.043 |
| | m/m | 0.022 | <0.0011 |
| HIV-1WRM$_{8488}$ | m/m | 0.028 | <0.0011 |

EXAMPLE 11

Toxicity Evaluation

The cellular toxicity of the compounds were assessed on various cells using [$^3$H]-thymidine uptake. Various cells, including Molt-4, HT1080, DU-145, HepG-2 and HSF, were plated at a concentration of 1–2×10$^3$ cells per well (96 well plates). After a 24 hr incubation period, 10-fold serial diluted compounds (10$^{-4}$ M to 10$^{-10}$ M) were added to the culture medium and the cells were further incubated for 72 hrs. [$^3$H]-thymidine was added during the final 18 hr incubation period. After incubation with the [$^3$H]-thymidine, the cells were washed once with PBS, treated with trypsin if the cells were adherent, and then resuspended in water (hypotonic lysing of cells). The cellular extract was applied directly to a Tomtec Harvester 96. Using this instrument the extracted DNA is adsorbed onto filters, washed and the incorporated [$^3$H]-thymidine is then counted. The 50% cytotoxic concentration (CC$_{50}$) was determined by comparing the radioactive counts per minute of the samples in the presence of the compounds against the control. The cellular toxicity of the compounds was also tested by WST-1 staining through assessing proliferation of MT-2, H9, Jurkat, U937, and CBMCs. The established cell lines were cultured in RPMI medium in 96-well plates at a density of 5×10$^4$ cells/well while CBMCs were plated at a concentration of 0.5×10$^6$/ well. A 10-fold serial diluted (10$^{-4}$–10$^{-7}$ M) compound was added at day zero. At day 4, the cells were passaged by changing half medium containing appropriately diluted compound. The cell activities were assessed at day 7 using the WST-1 reagent (Boehringer Mannheim) following the protocol provided by the supplier. The results are reported in table 4.

EXAMPLE 12

Preliminary Pharmacokinetic Studies

The bioavailability of the compounds were evaluated in male adult rats dosed intravenously through the tail vein (5 mg/kg) and orally (20 mg/kg). The plasma samples were collected at 2, 5, 15, 30, 60, 90, 120 and 240 minutes after intravenous dosing and 5, 15, 30, 60, 90, 120, 240 and 360 minutes after oral dosing.

Experimental Procedures

Plasma preparation

Blood samples (1 ml) were collected from the rat tails into a vacutainer containing EDTA (3 ml) for both iv and po administrations. Plasma samples were prepared by centrifugation at 2000 xg for 15 minutes at 4° C.

HPLC analysis

Analytical onditions:

HPLC system: Two Waters 616 pump systems and two Alliance 2690 systems with PDA 996, Column: Phenomenex Luna C18 (2), 5 $\mu$m, 250*4.6 mm, Gradient: 0–35% solvent A in 20 minutes. Solvent A contains acetonitrile with 0.01% TFA and solvent B contains Millipore water (0.25 $\mu$m filter) with 0.01% TFA, Flow rate: 1.0 ml/min, UV: 200–350 nm Solid Phase Extraction:

Plasma samples (diluted to 1 ml with water) were loaded onto the Abselut Nexus sorbent (# 1210–3100) and drawn through under low vacuum (approximately 5" Hg). One milliliter of deionized water was added to the sorbent and drawn through under vacuum. The extraction column was dried for 1 minute using a high vacuum (>10" Hg). One milliliter of methanol was added to the Abselut Nexus column and the eluent was collected at 1–2 ml/min. The eluent was evaporated to dryness using a Speed Vac, and the samples were reconstituted in 120 $\mu$l H2O; 100 $\mu$l was used for injection. The results are reported in table 5.

TABLE 4

| | Toxicity. | | | | | | | |
|---|---|---|---|---|---|---|---|---|
| | | CC50 ($\mu$M) | | | | | | |
| | WST-1 | [$^3$H-]TTP incorporation in: | | | | | | Mice* |
| Compound | CBMC | PBMC | Molt-4 | HT1080 | U-145 | HepG2 | HSF | (50 mg/kg/d) |
| DXG | >100 | >500/250 | >500/250 | >500/250 | >500/250 | >500/250 | ≧500 | No |
| DAPD | >100 | >500 | >500 | >500 | >500 | ≧500 | 500/350 | No |
| Cmpd B (−) | >100 | 80/90 | >250 | >250 | 200 | >250 | — | No |
| Cmpd C (−) | >100 | — | — | — | >10 | — | — | No |
| Zidovudine | 74 | — | 3 | 5 | >10 | 3 | >10 | — |
| Lamivudine | ND | — | >100 | >500/100 | >500/100 | 350/100 | 400 | — |
| Zalcitabine | 29 | 50/15 | 2 | 2 | 5 | 7 | — | — |

*Body weight gaining effect administered intraperitoneally in mice (CDI, adult, male) at a dose of 50 mg/kg/day for 5 days.

TABLE 5

PK and oral bioavailability.

| Compound | Administration (mg/kg) | Animal | Oral BA (%) | AUC (μg/ml. hr) | T1/2 (hr) | Cmax (μg/ml) |
|---|---|---|---|---|---|---|
| DXG | oral, 20 | rat | 4.43 ± 1.65 | 0.91 ± 0.34 | 2.45 ± 0.59 | 0.27 ± 0.03 |
|  | iv, 5 | rat | — | 5.15 | 0.62 | 29.02 |
| DAPD | oral, 20 | rat | 7.42 ± 1.58 | 1.89 ± 0.40 | 0.77 ± 0.31 | 1.04 ± 0.24 |
| Cmpd A (−) | oral, 20 | rat | 45.56 ± 2.78 | 8.64 ± 0.53 | 0.64 ± 0.24 | 4.20 ± 0.65 |
|  | iv, 5 | rat | — | 4.74 | 0.37 | 14.26 |
| Cmpd B (−) | oral, 20 | rat | 13.75 | 3.08 | 1.20 | 1.12 |
|  | iv, 5 | rat | — | 5.60 | 0.31 | 13.26 |
| Cmpd C (−) | oral, 20 | rat | 4.58 | 0.44 | 0.31 | 0.67 |
|  | iv, 5 | rat | — | 2.40 | 0.32 | 14.53 |

EXAMPLE 14

Drug Resistant Profiles of the Compound A (−)

Recombinant HIV-1 variants were prepared by introducing the designed mutations into HXB2-D by site-directed mutagenesis as described (Gu et al. 1992, 1994). The virus stocks were prepared by transfecting MT-4 cells with infectious viral DNA constructs. Antiviral activity of the compound A (−) was evaluated as described in example 10. The compound A (−) had slightly decreased activity against HIV-1 variants carrying K65R and/or M184V mutation in reverse transcriptase, but remained sensitive to other variants which were resistant to zidovudine, non-nucleoside inhibitors and protease inhibitors (Table 6).

TABLE 6

Efficacy of the compound A (−) to recombinant drug resistant HIV-1 variants (determined by RT activity)

| Virus (no. determinations) | RT genotype | $EC_{50}$ (μM) Compound A (−) | Zidovudine | Lamivudine |
|---|---|---|---|---|
| HXB2-D (2) | wt | 0.53 | 0.023 | 0.35 |
| K65R (2) | 65R | 1.03 | 0.021 | 4.31 |
| L74V (2) | 74V | 0.62 | 0.010 | 0.51 |
| M184V (2) | 184V | 0.53 | 0.02 | >40 |
| M184I | 184I | 0.99 | 0.009 | >40 |
| K65R/ M184V (3) | 65R, 184V | 1.1 | 0.031 | >40 |
| E89G/ M184V (2) | 89G, 184V | 0.51 | 0.022 | >40 |
| JM1 (1) | 41L, 184V, 215Y | 1.83 | 0.027 | >40 |
| JM4 (2) | 41L, 70R, 215Y, 219Q | 0.58 | 0.27 | 0.85 |
| NNRTI[R,1] (1) | 106A, 181C | 0.10 | 0.0061 | 0.15 |
| PI[R,2] (2) | 10R, 46I, 63P, 82T 84V (protease genotype) | 0.20 | 0.017 | 0.29 |

[1]$EC_{50}$ for nevirapine was >10 μM.
[2]$EC_{50}$ for saquinavir was 0.028 μM. $EC_{50}$ of wt HXB2-D for saquinavir was 0.0015 μM.

EXAMPLE 15

Efficacy of the Compound A (−) Against Clinical HIV-1 Isolates

Clinical strains were isolated from PBMCs of HIV-1 infected individuals through co-culture with PBMCs from normal dornors. To determine the RT genotype of the HIV-1 clinical isolates, the proviral DNA was extracted from infected CD4+ T-cells or PBMCs and the complete RT coding regions were amplified by PCR as previously reported (Gu et al 1992). The PCR product was purified and then directly sequenced using primer RTS (5'-CCAAAAGTTAAACAATGGC-3') which is located at the 5' portion of the RT coding region (nucleotide 2603–2621 of HXB2-D coordinates). Antiviral activity was evaluated as described in example 10.

TABLE 7

Activity of the compound A (−) against clincial HIV-1 isolates (determined by RT activity)

| Virus (No. isolates) | $EC_{50}$ (μM) Compound A (−) | Zidovudine | Lamivudine |
|---|---|---|---|
| Zidovudine[S(a)]/ Lamivudine[S] (7) | 0.15[(b)] (0.032–0.31)[(b)] | 0.021 (0.0034–0.051) | 0.23 (0.028–0.69) |
| Zidovudine[S]/ Lamivudine[R] (3) | 0.38 (0.13–0.51) | 0.012 (0.0026–0.019) | — (5.1–>10) |
| Zidovudine[R]/ Lamivudine[S] (3) | 0.19 (0.066–0.33) | 0.83 (0.25–1.74) | 0.25 (0.096–0.34) |
| Zidovudine[R]/ Lamivudine[R] (2) | 0.33 (0.27/0.39) | 1.15 (0.49/1.81) | 4.1 (3.6/4.6) |

[(a)]S represents sensitive, R represents resistant.
[(b)]Mean $EC_{50}$ values.
[(c)]Ranges of $EC_{50}$s of the isolates in the same group.

TABLE 8

Activity of the compound A (−) against drug-resistant clinical isolates in PBMCs (determined by p24)

| Isolates | $IC_{50}$ (μM) Compound A (−) | Lamivudine | Zidovudine | Abacavir | Adefovir | Stavudine |
|---|---|---|---|---|---|---|
| 105/A (wt) | 0.6 | 0.065 | 0.0043 | <0.03 | 2.0 | 0.063 |
| CCR15 (Lamivudine[R*]) | 0.3 | 95 | 0.003 | 0.22 | 0.8 | 0.06 |
| CCR18 (Lamivudine[R]) | 1.3 | 300 | 0.0042 | 1.3 | 2.1 | 0.049 |
| CCR19 (Lamivudine[R]) | 1.6 | 95 | 0.003 | 0.58 | 2.3 | 0.05 |
| 105/F (zidovudine[R]) | 0.84 | 0.17 | 0.23 | 0.07 | 7.0 | 0.12 |

*[R]represents resistant

EXAMPLE 16

Drug Combination Effects

Combination effects of the compound A () with anti-HIV-1 agents were assessed in MT-2 or PBMCs using HIV-1$_{IIIB}$. The combinations were performed using a checker board cross pattern of drug concentrations. The antiviral effects were determined by monitoring RT activity in the culture supernatants. The data were analyzed according to the method described by Chou and Talalay (Chou and Talalay, 1984) and Prichard (Prichard et al., 1993). The combination indexes (CIs) of the compound A (−) with other anti-HIV-1 agents were calculated using a CalcuSyn software (Biosoft, Cambridge, UK). Theoretically, a CI value of 1 indicates an additive effect, a CI value of >1 indicates antagonism and a CI value of <1 indicates synergism. MacSynergy II software was used to calculate synergy or antagonist volumnes for the drug combination.

TABLE 9

Combination effect of Compound A (−) and Zidovudine in MT-2 cells

| Molar ratio | CIs at: | | | MacSynergy ($\mu M^2\%$) (95% confidence) |
|---|---|---|---|---|
| | $EC_{50}$ | $ED_{75}$ | $EC_{95}$ | |
| Compound A (−): AZT | | | | |
| 5:1 | 0.92 | 0.96 | 1.03 | |
| 10:1 | 0.64 | 0.70 | 0.82 | |
| 20:1 | 0.27 | 0.37 | 0.63 | |
| 40:1 | 0.20 | 0.23 | 0.31 | |
| | | | | 69.3 |

TABLE 10

Combination effect of Compound A (−) and AZT (zidovudine) in PBMCs

| Molar ratio | CIs at: | | | MacSynergy ($\mu M^2\%$) (95% confidence) |
|---|---|---|---|---|
| | $EC_{50}$ | $ED_{75}$ | $EC_{95}$ | |
| Compound A (−): AZT | | | | |
| 1.1:1 | 0.84 | 0.74 | 0.61 | |
| 3.33:1 | 0.49 | 0.53 | 0.63 | |
| 10:1 | 0.40 | 0.37 | 0.37 | |
| 30:1 | 0.40 | 0.27 | 0.16 | |
| | | | | 17.03 |

TABLE 11

Combination effect of Compound A (−) and (Lamivudine) in MT-2 cells

| Molar ratio | CIs at: | | | MacSynergy ($\mu M^2\%$) (95% confidence) |
|---|---|---|---|---|
| | $EC_{50}$ | $ED_{75}$ | $EC_{95}$ | |
| Compound A (−) Lamivudine | | | | |
| 1:2 | 0.80 | 0.85 | 0.95 | |
| 1:1 | 0.78 | 0.74 | 0.68 | |
| 2:1 | 0.81 | 0.78 | 0.73 | |
| 4:1 | 0.91 | 0.96 | 1.06 | |
| | | | | −7.89/−11.6 |

TABLE 12

Combination effect of Compound A(−) and Stavudine (d4T) in MT-2 cells

| Molar ratio | CIs at: | | | MacSynergy ($\mu M^2\%$) (95% confidence) |
|---|---|---|---|---|
| | $EC_{50}$ | $EC_{75}$ | $EC_{95}$ | |
| Compound A(−): d4T | | | | |
| 1:4 | 0.61 | 0.55 | 0.68 | |
| 1:2 | 0.75 | 0.79 | 1.07 | |

TABLE 12-continued

Combination effect of Compound A(−) and Stavudine (d4T) in MT-2 cells

| Molar ratio | CIs at: | | | MacSynergy ($\mu M^2\%$) (95% confidence) |
|---|---|---|---|---|
| | $EC_{50}$ | $EC_{75}$ | $EC_{95}$ | |
| 2:1 | 0.68 | 0.64 | 0.65 | |
| | | | | 2.81/−5.64 |

TABLE 13

Combination effect of Compound A(−) and nevirapine in MT-2 cells

| Molar ratio | CIs at: | | | MacSynergy ($\mu M^2\%$) (95% confidence) |
|---|---|---|---|---|
| | EC50 | EC75 | EC95 | |
| Compound A(−): nevirapine | | | | |
| 5:1 | 0.81 | 0.78 | 0.77 | |
| 10:1 | 0.68 | 1.0 | 1.14 | |
| 20:1 | 0.86 | 0.99 | 1.04 | |
| | | | | −0.73 |

EXAMPLE 17

Cytotoxicity Analysis

Cellular toxicity was assessed by [$^3$H]thymidine uptake (de Muys et al. 1999) and WST-1 staining. In the [$^3$H] thymidine uptake experiments, Molt-4, HT1080, DU-145, HepG2 and HSF, were plated at a concentration of 1–2×10$^3$ cells per well (96 well plates). PHA-stimulated PBMCs were cultured at a concentration of 4×10$^4$ cells per well. Following a 24 hr pre-incubation period, test compounds ($10^{-4}$ M to $10^{-10}$ M) were added and the cells were incubated for an additional 72 hrs. [$^3$H]thymidine was added during the final 18 hr incubation period. The cells were then washed once with PBS, treated with trypsin if the cells were adherent, and resuspended in water (hypotonic lysing of cells). The cellular extract was applied directly to a Tomtec Harvester 96. The 50% cytotoxic concentration ($CC_{50}$) was determined by comparing the radioactive counts per minute obtained from drug-tested samples to those obtained from the control (untreated) cells.

In the WST-1 staining experiments, cell lines were cultured in RPMI medium in 96-well plates at a density of 5×10$^4$ cells/well. CBMCs were plated at a concentration of 0.5×10$^6$/well. Compounds ($10^{-4}$–$10^{-7}$ M) were added at day zero. Cell viability was assessed on day 7 using the WST-1 reagent (Boehringer Mannheim) following the protocol provided by the supplier.

The compound A (−) had much less cytotoxicity than both zidovudine and zalcitabine in the different types of cells assessed by both [$^3$H]thymidine incorporation and WST-1 staining (Table 14).

TABLE 14

Cytotoxicity of the compound A (−)

| Com-pound | WST-1 | | [³H]TTP incorporation in: | | | | |
|---|---|---|---|---|---|---|---|
| | CBMC | PBMC | Molt4 | HT800 | U145 | HepG2 | HSF |
| Compound A (−) | >100 | 286 | >500 | >500 | >500 | >500 | 414 |
| Zidovudine | 74 | 9 | 3 | 5 | >10 | 3 | >10 |
| Lamivudine | ND | >500 | >100 | >500 | >500 | >100 | 400 |
| Zalcitabine | 29 | 35.5 | 1 | 2.5 | 3.5 | 6.5 | 2 |

CC$_{50}$ ($\mu$M)

EXAMPLE 18

Mitochondria DNA Toxicity Assay

Mitochondria DNA (mtDNA) toxicity of the compound A (−) was tested in HepG2 cells. The cells were cultured for 28 days under the compound treatment. Th cells were passaged once a week. However, the cell culture medium containing proper concentration of the compound was changed twice a week. Zalcitabine was used as a control. The toxicity was determined by measuring content ratio of mtDNA and nuclear DNA (28s rDNA) by a southern hybridization assay (de Muys et al., 1999). The compound A (−) did not show significant mtDNA toxicity up to 100 $\mu$M, the highest concentration tested (FIG. 1).

EXAMPLE 19

Pharmacokinetic Study of the Compounds of the Invention

Compound A(−), DAPD, and DXG were administrated as a single dose, either intravenously through the jugular vein at 10 mg/kg or orally at 20, 125, 500, 1000 or 2000 mg/kg. All rats were fasted for 12 hours prior to po dosing treatment. The vehicle used for both iv and po administrations was 0.1% carboxymethylcellulose and 0.1% Tween 80 in distilled water, acidified to pH 3.15 with 1N HCl. Blood samples were taken from rats at the times shown in the schedule below for all oral dosing. From a total of 10 rats for each administration, seven time points were taken for the intravenous through the jugular vein dosing (2, 5, 15, 30, 60, 120 and 240 min) and for the oral dosing (5–360 min) at 20 mg/kg, whereas two additional time points at 480 and 1440 min were taken for the oral doses of 125–2000 mg/kg. As a result, each time point was in quadruplicate, except for the 1440 minute time point when blood samples were taken through the jugular vein from all the rats prior to being euthanized.

Schedule of blood sampling for rats dosed orally

| Time (min) | 5 | 15 | 30 | 60 | 120 | 240 | 360 | 480 | 1440 |
|---|---|---|---|---|---|---|---|---|---|
| Rat 1 | x | | x | | | x | | | x |
| Rat 2 | | x | | x | | x | | | x |
| Rat 3 | x | x | | | x | | | x | x |
| Rat 4 | | | x | x | | x | | x | x |
| Rat 5 | | x | | x | x | | | | x |
| Rat 6 | x | | x | | x | | | x | x |
| Rat 7 | | x | | x | | | | x | x |
| Rat 8 | x | | x | | | | x | | x |
| Rat 9 | | x | | x | x | | | | x |
| Rat 10 | | x | x | | | | x | | x |

Plasma was prepared from approximately 1 ml blood taken at each time point from each rat.

Experimental Procedures

Plasma preparation

Blood samples (1 ml) were collected from the rat tails into a vacutainer containing EDTA (3 ml) for both iv and po administrations. Plasma samples were prepared by centrifugation at 2000×g for 15 minutes at 4° C.

HPLC analysis

Analytical conditions:

HPLC system: Two Waters 616 pump systems and two Alliance 2690 systems with PDA 996, Column: Phenomenex Luna C18 (2), 5 $\mu$m, 250*4.6 mm, Gradient 0–35% solvent A in 20 minutes. Solvent A contains acetonitrile with 0.01% TFA and solvent B contains Millipore water (0.25 $\mu$m filter) with 0.01% TFA, Flow rate: 1.0 ml/min, UV: 200–350 nm Solid Phase Extraction:

Plasma samples (diluted to 1 ml with water) were loaded onto the Abselut Nexus sorbent (#1210–3100) and drawn through under low vacuum (approximately 5" Hg). One milliliter of deionized water was added to the sorbent and drawn through under vacuum. The extraction column was dried for 1 minute using a high vacuum (>10" Hg). One milliliter of methanol was added to the Abselut Nexus column and the eluent was collected at 1–2 ml/min. The eluent was evaporated to dryness using a Speed Vac, and the samples were reconstituted in 120 $\mu$l H2O; 100 $\mu$l was used for injection. The results are reported in table 15 and 16.

TABLE 15

PK parameters for Compound A (−) following iv (10 mg/kg) or po (20 mg/kg) administration in rats

| Rat | Male | | Female | |
|---|---|---|---|---|
| Route | iv | po | iv | po |
| Dose (mg/kg) | 10 | 20 | 10 | 20 |
| Sample size | 4 | 4 | 4 | 4 |
| C$_{max}$ ($\mu$g/ml) | 19.2 | 4.6 | 22.9 | 5.5 |
| T$_{max}$ (min) | — | 23.4 | — | 22.8 |
| T-half elimination (min) | 34.2 | 72.5 | 36.9 | 57.1 |
| AUG ($\mu$g.min/ml) | 304 | 600 | 328 | 602 |
| Bioavailability (%) | — | 99 | — | 92 |

TABLE 16

Pharmacokinetic parameters of DAPD & DXG in male and female rats after iv or po administration of DAPD

| Parameter | Female | | Male | |
|---|---|---|---|---|
| Route | iv (10 mg/kg) | po (20 mg/kg) | iv (10 mg/kg) | po (20 mg/kg) |

TABLE 16-continued

Pharmacokinetic parameters of DAPD & DXG in male and female rats after iv or po administration of DAPD

| Parameter | Female | | Male | |
|---|---|---|---|---|
| Cmax (µg/ml) | 22.1 | 2.5 | 16.2 | 1.96 |
| Tmax (min) | — | 45 | — | 35 |
| $T_{1/2}$ | 31.5 | 31.3 | 36.2 | 34 |
| AUC (µg*min/ml) | 357.9 | 307.2 | 271.2 | 196.5 |
| Cl (ml/min) | 6.6 | 13.7 | 9.5 | 23.6 |
| Bioavailability (%) | | 43 | | 36 |

Below are the complete references cited in the throughout the application:

1. De Muys, J. -M., H. Gourdeau, N. Nguyen-Ba, D. T. Taylor, P. S. Ahmed, T. Mansour, C. Locas, N. Richard, M. A. Wainberg, and R. F. Rando. 1999. Anti-human immunodeficiency virus type 1 activity, intracellular metabolism, and pharmacokinetic evaluation of 2'-deoxy-3'-oxa-4'-thiocytidine. Antimicrob. Agents Chemother. 43:1835–1844.
2. Gu, Z., Q. Gao, M. A. Parniak, and M. A. Wainberg. 1992. Novel mutation in the human immunodeficiency virus type 1 reverse transcriptase gene that encodes cross-resistance to 2',3'-dideoxyinosine and 2',3'-dideoxycytidine. J. Virol. 66:12–19.
3. Gu, Z., Q. Gao, H. Fang, H. Salomon, M. A. Parniak, E. Goldberg, J. Cameron, and M. A. Wainberg. 1994a. Identification of a mutation at codon 65 in the IKKK motif of reverse transcriptase that encode human immunodeficiency virus resistance to 2',3'-dideoxycytidine and 2',3'-dideoxy-3'-thiacytidine. Antimicrob. Agents Chemother. 38:275–281.
4. Gu, Z., M. A. Wainberg, N. Nguyen-Ba, L. L'Heureux, J. -M. de Muys, T. L. Bowlin, and R. F. Rando. 1999. Mechanism of action and in vitro activity of 1',3'-dioxolanylpurine nucleoside analogues against seneitive and drug-resistant human immunodeficiency virus type 1 variants. 43:2376–2382.
5. Chou, T. C., and p Talalay. 1984. Quantitative analysis of dose effect relationships: the combined effects of multiple drugs or enzyme inhibitors. Adv. Enzyme Regul. 22:27–55.
6. Prichard, M. N., L. E. Prichard, and C. Shipman, Jr. 1993. Strategic design and three-dimentional analysis of antiviral drug combinations. Antimicrob. Agents Chenmother. 37:540–545.
7. Rando, R., J. Ojwang, A. Elbaggari, G. R. Reyes, R. Tinder, M. S. McGrath, and M. E. Hogan. 1995. Suppression of human immunodeficiency virus type 1 activity in vivo by oligonucleotide which form intramolecular tetrads. J. Biol. Chem. 270:1754–1760.
8. Salomon, H., A. Belmonte, K. Nguyen, Z. Gu, M. Gelfand, and M. A. Wainberg. 1994. Comparison of cord blood and peripheral blood mononuclear cells as targets for viral isolation and drug sensitivity studies involving human immunodeficiency virus type 1. J. Clin. Microbiol. 32:2000–2002.

What is claimed is:

1. A compound wherein said compound is a cis-nucleoside of formula (I):

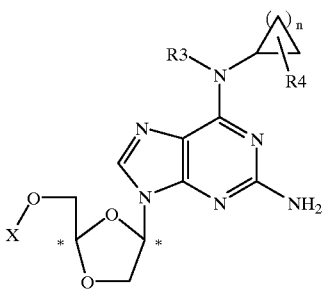

(I)

or a pharmaceutically acceptable salt thereof,
wherein:
n is 1 or 2;
$R_4$ is H, COOH, CONH$_2$, OH, SH, NH$_2$, NO$_2$, $C_{1-6}$ alkyl, $C_{2-6}$ alkenyl, $C_{2-6}$ alkynyl, halogen, or COR$_a$;
$R_a$ is a $C_{1-6}$ alkyl, $C_{2-6}$ alkenyl, $C_{2-6}$ alkynyl or COOR$_b$;
$R_b$ is a $C_{1-6}$ alkyl, $C_{2-6}$ alkenyl or $C_{2-6}$ alkynyl;
$R_3$ is H or a $C_{1-6}$ alkyl, $C_{2-6}$ alkenyl, or $C_{2-6}$ alkynyl;
X is H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, or

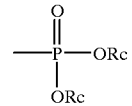

Rc is in each case independently, H, $C_{1-6}$ alkyl, $C_{2-6}$ alkenyl, $C_{2-6}$ alkynyl or a hydroxy protecting group selected from acetyl-2-thioethyl ester, pivaloyloxymethyl ester and isopropyloxycarbonyloxymethyl ester; and
wherein said nucleoside is present in the (−) enantiomer form and is at least 95% free of the (+) enantiomer form.
2. A compound according to claim 1 wherein said nucleoside is present in the (−) form and is at least 97% free of the (+) form.
3. A compound according to claim 1 wherein said nucleoside is present in the (−) form and is at least 99% free of the (+) form.
4. A compound according to claim 1 wherein X is H.
5. A compound according to claim 1 wherein n is 1.
6. A compound according to claim 5, wherein $R_3$ is H or $C_{1-6}$ alkyl.
7. A compound according to claim 6, wherein $R_4$ is H, COOH, CONH$_2$, $C_{1-6}$ alkyl, $C_{2-6}$ alkenyl, $C_{2-6}$ alkynyl or COOR$_b$, and $R_b$ is $C_{1-6}$ alkyl, $C_{2-6}$ alkenyl, or $C_{2-6}$ alkynyl.
8. A compound according to claim 6, wherein $R_4$ is H, COOH, or $C_{1-6}$ alkyl.
9. A compound according to claim 6, wherein $R_4$ is methyl or ethyl.
10. A compound according to claim 6, wherein $R_4$ is COOH.
11. A compound according to claim 6, wherein $R_3$ and $R_4$ are H.
12. A combination useful for the treatment of viral infections comprising at least one compound according to claim 1 or pharmaceutically acceptable salts thereof comprising at least one further therapeutic agent chosen from nucleoside analogues; NNRTIs; or protease inhibitors.

13. The combination of claim 12 wherein the nucleoside analogue is chosen from zidovudine, didanosine, zalcitabine, stavudine or lamivudine.

14. The combination of claim 12 wherein the non-nucleoside reverse transcriptase inhibitor is chosen from nevirapine, delavirdine or efavirenz.

15. The combination of claim 12 wherein the protease inhibitor is chosen from indinavir, nelfinavir, saquinavir or ritonavir.

16. A method for the treatment of viral infections comprising administering a therapeutically effective amount of a compound according to claim 1 to a subject in need of such treatment.

17. The method according to claim 16, wherein the viral infection is an HIV infection.

18. The method according to claim 17 wherein the viral infection is an HBV infection.

19. A pharmaceutical formulation comprising at least one compound according to claim 1 together with at least one pharmaceutically acceptable carrier or excipient.

20. A method according to claim 16, wherein said compound is administered in an amount of 0.1–750 mg/kg of body weight per day.

21. A method according to claim 16, wherein said compound is administered in an amount of 0.5–60 mg/kg of body weight per day.

22. A method according to claim 16, wherein said compound is administered in an amount of 1–20 mg/kg of body weight per day.

23. A method according to claim 17, wherein said compound is administered in an amount of 0.1–750 mg/kg of body weight per day.

24. A method according to claim 18, wherein said compound is administered in an amount of 0.1–750 mg/kg of body weight per day.

25. A method according to claim 20, wherein $R_3$ is H or $C_{1-6}$ alkyl.

26. A method according to claim 20, wherein $R_4$ is H, COOH, CONH$_2$, $C_{1-6}$ alkyl, $C_{2-6}$ alkenyl, $C_{2-6}$ alkynyl or COOR$_b$, and R$_b$ is $C_{1-6}$ alkyl, $C_{2-6}$ alkenyl, or $C_{2-6}$ alkynyl.

27. A method according to claim 20, wherein $R_4$ is H, COOH, or $C_{1-6}$ alkyl.

28. A method according to claim 20, wherein $R_4$ is methyl or ethyl.

29. A method according to claim 20, wherein $R_4$ is COOH.

30. A method according to claim 20, wherein $R_3$ and $R_4$ are H.

31. A method according to claim 20, wherein said compound is cis-2-hydroxymethyl-4-(2'-amino-6'-cyclopropylamino-purine-9'-yl)-1,3-dioxolane or a pharmaceutically acceptable salt thereof.

32. A method according to claim 20, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof.

33. A method according to claim 20, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof, and which is at least 97% free of the corresponding (+) enantiomer.

34. A method according to claim 23, wherein said compound is cis-2-hydroxymethyl-4-(2'-amino-6'-cyclopropylamino-purine-9'-yl)-1,3-dioxolane or a pharmaceutically acceptable salt thereof.

35. A method according to claim 23, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof.

36. A method according to claim 23, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof, and which is at least 97% free of the corresponding (+) enantiomer.

37. A method according to claim 24, wherein said compound is cis-2-hydroxymethyl-4-(2'-amino-6'-cyclopropylamino-purine-9'-yl)-1,3-dioxolane or a pharmaceutically acceptable salt thereof.

38. A method according to claim 24, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof.

39. A method according to claim 24, wherein said compound is (−)-(2R, 4R)-2-hydroxymethyl-4-(2'-amino-6'-cyclopropylamino-purine-9'-yl)-1,3-dioxolane or a pharmaceutically acceptable salt thereof, and which is at least 97% free of the corresponding (+) enantiomer.

40. A method according to claim 20, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

41. A method according to claim 23, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

42. A method according to claim 24, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

43. A method according to claim 31, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

44. A method according to claim 32, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

45. A method according to claim 33, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

46. A method according to claim 34, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

47. A method according to claim 35, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

48. A method according to claim 36, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

49. A method according to claim 37, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

50. A method according to claim 38, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

51. A method according to claim 39, further comprising administering to said subject at least one further therapeutic agent chosen from nucleoside analogues, non-nucleoside reverse transcriptase inhibitors, and protease inhibitors, wherein said at least one compound and said at least one further therapeutic agent are administered either sequentially or simultaneously in separate or combined formulations.

52. A method according to claim 40, wherein said at least one further therapeutic agent is zidovudine, didanosine, zalcitabine, stavudine, lamivudine, nevirapine, delavirdine, efavirenz, indinavir, nelfinavir, saquinavir or ritonavir.

53. A method according to claim 41, wherein said at least one further therapeutic agent is zidovudine, didanosine, zalcitabine, stavudine, lamivudine, nevirapine, delavirdine, efavirenz, indinavir, nelfinavir, saquinavir or ritonavir.

54. A method according to claim 42, wherein said at least one further therapeutic agent is zidovudine, didanosine, zalcitabine, stavudine, lamivudine, nevirapine, delavirdine, efavirenz, indinavir, nelfinavir, saquinavir or ritonavir.

55. A method according to claim 43, wherein said at least one further therapeutic agent is zidovudine, didanosine, zalcitabine, stavudine, lamivudine, nevirapine, delavirdine, efavirenz, indinavir, nelfinavir, saquinavir or ritonavir.

56. A method according to claim 44, wherein said at least one further therapeutic agent is zidovudine, didanosine, zalcitabine, stavudine, lamivudine, nevirapine, delavirdine, efavirenz, indinavir, nelfinavir, saquinavir or ritonavir.

57. A method according to 45, wherein said at least one further therapeutic agent is zidovudine, didanosine, zalcitabine, stavudine, lamivudine, nevirapine, delavirdine, efavirenz, indinavir, nelfinavir, saquinavir or ritonavir.

58. A method according to claim 46, wherein said at least one further therapeutic agent is zidovudine, didanosine, zalcitabine, stavudine, lamivudine, nevirapine, delavirdine, efavirenz, indinavir, nelfinavir, saquinavir or ritonavir.

59. A method according to claim 47, wherein said at least one further therapeutic agent is zidovudine, didanosine, zalcitabine, stavudine, lamivudine, nevirapine, delavirdine, efavirenz, indinavir, nelfinavir, saquinavir or ritonavir.

60. A method according to claim 48, wherein said at least one further therapeutic agent is zidovudine, didanosine, zalcitabine, stavudine, lamivudine, nevirapine, delavirdine, efavirenz, indinavir, nelfinavir, saquinavir or ritonavir.

61. A method according to claim 49, wherein said at least one further therapeutic agent is zidovudine, didanosine, zalcitabine, stavudine, lamivudine, nevirapine, delavirdine, efavirenz, indinavir, nelfinavir, saquinavir or ritonavir.

62. A method according to claim 50, wherein said at least one further therapeutic agent is zidovudine, didanosine, zalcitabine, stavudine, lamivudine, nevirapine, delavirdine, efavirenz, indinavir, nelfinavir, saquinavir or ritonavir.

63. A method according to claim 51, wherein said at least one further therapeutic agent is zidovudine, didanosine, zalcitabine, stavudine, lamivudine, nevirapine, delavirdine, efavirenz, indinavir, nelfinavir, saquinavir or ritonavir.

64. A formulation according to claim 19, wherein said compound is present in an amount of 10–1500 mg.

65. A formulation according to claim 19, wherein said compound is present in an amount of 20–1000 mg.

66. A formulation according to claim 19, wherein said compound is present in an amount of 50–700 mg.

67. A formulation according to claim 64, wherein said at least one compound is cis-2-hydroxymethyl-4-(2'-amino-6'-cyclopropylamino-purine-9'-yl)-1,3-dioxolane or a pharmaceutically acceptable salt thereof.

68. A formulation according to claim 64, wherein said at least one compound is (−)-(2R, 4R)-2-hydroxymethyl-4-(2'-amino-6'-cyclopropylamino-purine-9'-yl)-1,3-dioxolane or a pharmaceutically acceptable salt thereof.

69. A formulation according to claim 64, wherein said at least one compound is (−)-(2R, 4R)-2-hydroxymethyl-4-(2'-amino-6'-cyclopropylamino-purine-9'-yl)-1,3-dioxolane or a pharmaceutically acceptable salt thereof, and which is at least 97% free of the corresponding (+) enantiomer.

70. A formulation according to claim 64, wherein $R_3$ is H or $C_{1-6}$ alkyl.

71. A formulation according to claim 64, wherein $R_4$ is H, COOH, $CONH_2$, $C_{1-6}$ alkyl, $C_{2-6}$ alkenyl, $C_{2-6}$ alkynyl or $COOR_b$, and $R_b$ is $C_{1-6}$ alkyl, $C_{2-6}$ alkenyl, or $C_{2-6}$ alkynyl.

72. A formulation according to claim 64, wherein $R_4$ is H, COOH, or $C_{1-6}$ alkyl.

73. A formulation according to claim 64, wherein $R_4$ is methyl or ethyl.

74. A formulation according to claim 64, wherein $R_4$ is COOH.

75. A formulation according to claim 64, wherein $R_3$ and $R_4$ are H.

76. A compound according to claim 4, wherein n is 1.

77. A compound according to claim 76, wherein $R_3$ is H or $C_{1-6}$ alkyl.

78. A compound according to claim 76, wherein $R_4$ is H, COOH, $CONH_2$, $C_{1-6}$ alkyl, $C_{2-6}$ alkenyl, $C_{2-6}$ alkynyl or $COOR_b$, and $R_b$ is $C_{1-6}$ alkyl, $C_{2-6}$ alkenyl, or $C_{2-6}$ alkynyl.

79. A compound according to claim 76, wherein $R_4$ is H, COOH, or $C_{1-6}$ alkyl.

80. A compound according to claim 76, wherein $R_4$ is methyl or ethyl.

81. A compound according to claim 76, wherein $R_4$ is COOH.

82. A compound according to claim 76, wherein $R_3$ and $R_4$ are H.

83. A combination useful for the treatment of viral infections comprising at least one compound according to claim 4 or pharmaceutically acceptable salts thereof comprising at least one further therapeutic agent chosen from nucleoside analogues; NNRTIs; or protease inhibitors.

84. A method for the treatment of viral infections comprising administering a therapeutically effective amount of a compound according to claim 4 to a subject in need of such treatment.

85. The method according to claim 84, wherein the viral infection is an HIV infection.

86. The method according to claim 84, wherein the viral infection is an HBV infection.

87. A pharmaceutical formulation comprising at least one compound according to claim 4 together with at least one pharmaceutically acceptable carrier or excipient.

* * * * *